Figure 1:
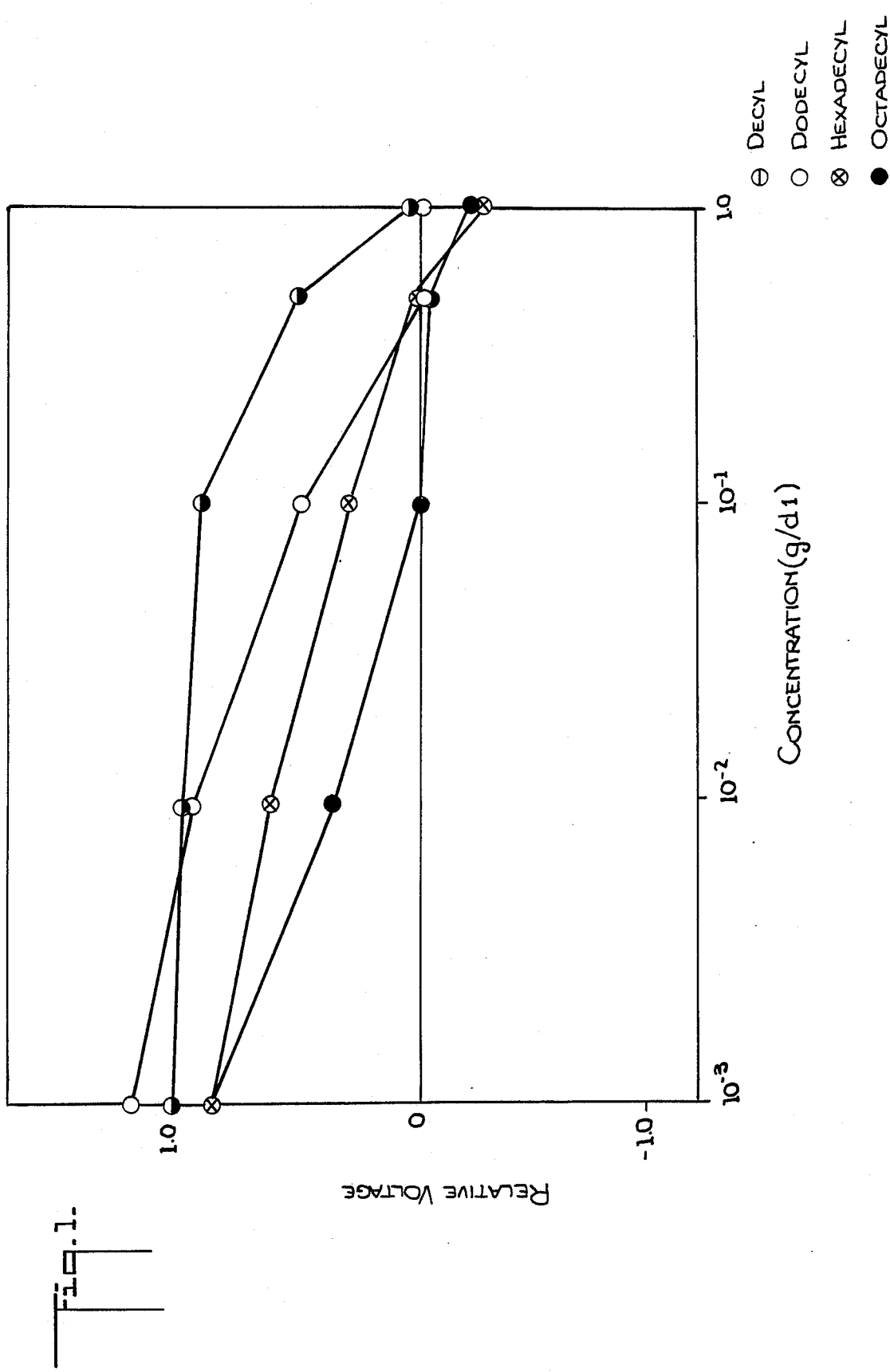

United States Patent [19]

Jachowicz et al.

[11] Patent Number: 4,818,245
[45] Date of Patent: Apr. 4, 1989

[54] PROCESS FOR TREATING PROTEIN FIBERS TO IMPART ANTISTATIC SURFACE MODIFICATIONS

[75] Inventors: Janusz Jachowicz, Stamford; Michael Wong, Easton, both of Conn.

[73] Assignee: Clairol Incorporated, New York, N.Y.

[21] Appl. No.: 1,722

[22] Filed: Jan. 9, 1987

[51] Int. Cl.$^4$ .................. A61K 7/06; D06M 00/00
[52] U.S. Cl. ......................... 8/188; 8/127.51; 252/8.8; 424/78; 424/70
[58] Field of Search .............. 8/127.5, 127.51, 188; 252/8.8; 424/70, 78

[56] References Cited

U.S. PATENT DOCUMENTS

| | | | |
|---|---|---|---|
| 4,371,517 | 2/1983 | Vanlerberghe | 424/70 |
| 4,416,297 | 11/1983 | Wolfram et al. | 132/7 |
| 4,597,962 | 7/1986 | Grollier et al. | 424/47 |
| 4,645,663 | 2/1987 | Grollier | 424/62 |

FOREIGN PATENT DOCUMENTS

| | | |
|---|---|---|
| 1419504 | 3/1969 | Fed. Rep. of Germany . |
| 2080759 | 2/1971 | France . |
| 2151049 | 4/1973 | France . |
| 2063671 | 6/1981 | United Kingdom . |

OTHER PUBLICATIONS

Jachowicz et al., Colloid & Polymer Sci., 263:847-858 (1985).
CTFA Cosmetic Ingredient Dictionary, 3rd Edition (1982), p. 245.

Primary Examiner—John F. Niebling
Assistant Examiner—Isabelle Rodriguez
Attorney, Agent, or Firm—Charles J. Zeller

[57] ABSTRACT

A process of imparting antistatic surface modifications to protein fibers by treating them with a polymeric high molecular weight quanternary ammonium salt having long chain organo groups as side chains which contain at least 12 carbon atoms in the chain.

15 Claims, 3 Drawing Sheets

☐ = PMAPTAC 1 g/dl
◐ = PHDPM .001 g/dl
○ = PHDPM .01 g/dl
● = PHDPM .1 g/dl
▲ = PVBI-PVHI .001 g/dl
▲ = PVBI-PVHI .01 g/dl
△ = PVBI-PVHI .1 g/dl

PROCESS FOR TREATING PROTEIN FIBERS TO IMPART ANTISTATIC SURFACE MODIFICATIONS

This invention relates to a process for imparting to protein fibers relatively durable antistatic surface modifications. More particularly, it concerns a process of this character that employs high molecular weight quaternary ammonium salt compositions also referred to herein as cationic polysoaps. The process has special utility in the treatment of human hair on the head.

It is known in the prior art, that when low molecular weight long chain alkyl quaternary ammonium salts are deposited on a keratin surface they provide both, an improvement in combability and an antistatic effect to this surface (A. C. Lunn, R. E. Evans, "The Electrostatic Properties of Human Hair," J. Soc. Cosmet. Chem., 28, 549 (1977). However, these effects are not durable since the low molecular weight quaternary salts are easily removed by shampooing. It is also known in the prior art, that cationic polymers are easily absorbed by the anionic keratin surface but are difficult to remove by rinsing or shampooing. Although there appears to be some opinion to the contrary, our experience has been that that keratin fibers treated with cationic polymers do not exhibit antistatic activity but in fact often show an increase in static change.

It has now been found that when cationic polysoaps are applied to a protein fiber surface, e.g. hair keratin surface, they serve to reduce static charge generation. Moreover, it has also been found that this effect is relatively durable in that it survives several rinsings or shampooing. Cationic polysoaps that are useful herein may be prepared by converting polymer containing tertiary amine groups to quaternary ammonium salts by treatment, for example, with a long chain organic halogen compound.

In the attached drawings:

FIG. 1: Is a graph of the relative voltage, after combing, of hair treated with a variety of alkyldimethylpropylmethacrylamide ammonium halide compounds versus the logarithm of treatment solution concentration; said compounds being applied from an aqueous solution. The alkyl groups of the compound are respectively, decyl◓, dodecyl◯, hexadecyl ⊗ and octadecyl ●.

Figure 2:
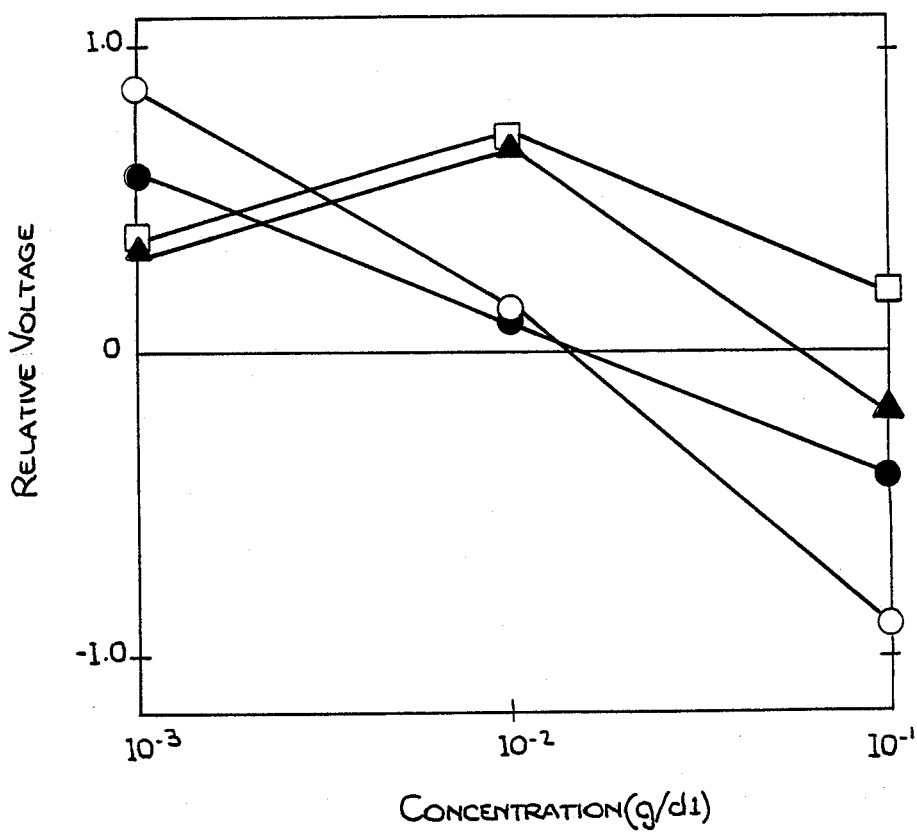

FIG. 2: Is a graph of relative voltage, after combing, of hair treated with a variety of poly(alkyldimethylpropylmethacrylamide ammonium halide) compounds as a function of the logarithm of the concentration of treatment solution; said compounds being applied from an ethanol solution. The alkyl groups of the compounds are respectively, decyl □, dodecyl ▲, tetradecyl ◯ and hexadecyl ◯.

Figure 3:
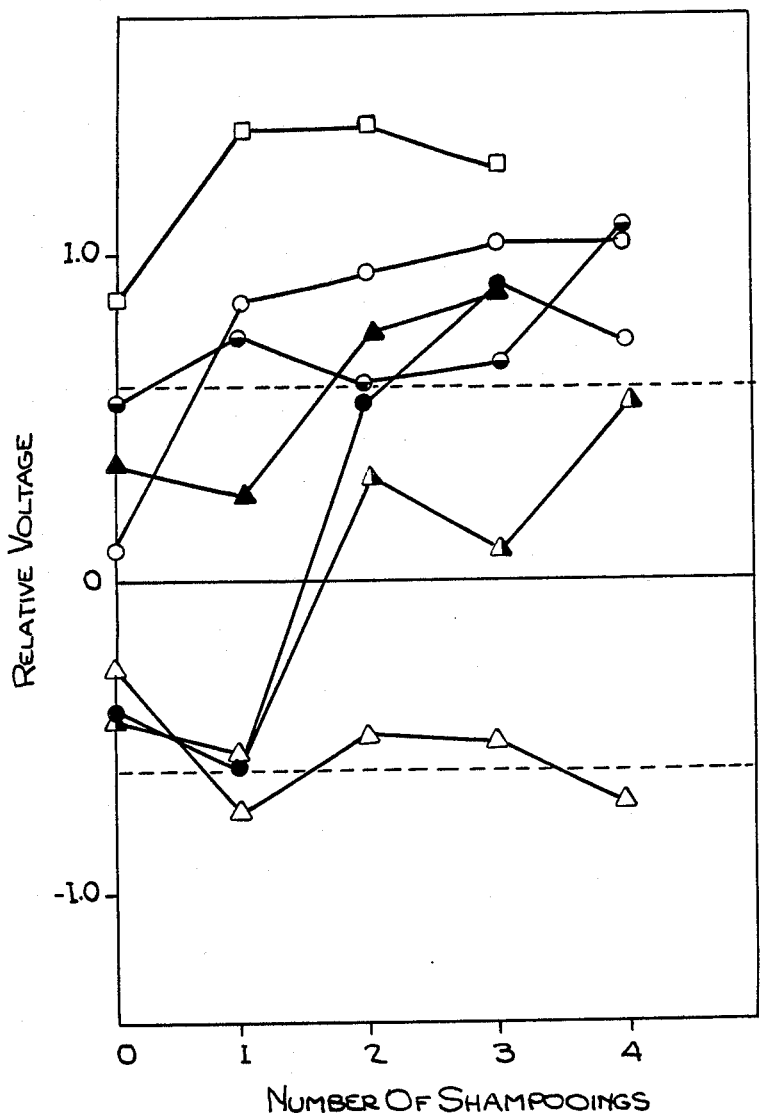

FIG. 3: Is a graph illustrating the durability of various polymer surface treatments. PHDPM applied at concentrations of 0.001 g/dl◓, 0.01 g/dl◯, and 0.1 g/dl ●; PVBI-PVHI applied at concentrations of 0.001 g/dl▲, 0.01 g/dl ▲

FIG. 3: and 0.1 g/dl Δ; and PMAPTAC at the concentration of 1 g/dl □; PHDPM, PBVI-PVHI and PMAPTAC having the significance hereinafter defined PHDPM, PVBI-PVHI being applied from ethanol solution and PMAPTC being applied from an aqueous solution.

With regard to the prior art:

U.S. patent to Melby U.S. Pat. No. 4,292,212 relates to shampoo-creme rinse compositions for improving combing properties and luster which comprise a single phase aqueous detergent composition containing an amphoteric detergent, an anionic detergent and a cationic derivative of 3(trimethylamino)-2-hydroxypropyl guar chloride salt. There is no teaching in this reference that these compositions impart antistatic characteristics to hair. Moreover, these compositions do not contain the polysoaps employed in the present invention.

Hannan et al U.S. Pat. No. 4,299,817 concerns an aqueous composition for setting hair which contains, as the active ingredient, a polyelectrolyte complex which is the ionic reaction product of one or more polycationic polymers and one or more polyanionic polymers. The polysoaps used in the present invention are not employed by Hannan et al nor do they disclose that the composition they employ affect the electrostatic properties of hair.

Grollin et al U.S. Pat. No. 4,240,450 teach the use of a combination of a cationic polymer and an anionic polymer for the treatment of human hair, skin and nails. According to this patent the cationic polymer is employed to improve the retention of the anionic polymer on the hair.

This is clearly different from the process of the present invention. Although Grollier et al suggest that quaternary polymers may be used as the cationic polymer component of their composition or process (column 8, line 45 et. seq.) they do not teach the special benefits that follow from the use of the polysoaps as is characteristic of the present invention.

The two U.S. Pat. Nos. 4,150,115 and 4,197,865 relate to composition containing quaternized polymers for treating hair. However, there is no suggestion for using such materials for reducing static charge on hair. Moreover, there is no particular disclosure for employing polysoaps in the process disclosed in these patents.

U.S. Pat. No. 4,157,388 relates to conditioning agents for skin, hair, textile products or powders which are said to be antistatic. Among the agents suggested for this purpose are the polyquaternary ammomium ionenes. However, there is no particular disclosure of the ionenes that contain long chain alkyl groups (i.e. the polysoaps) that are useful for the present purposes.

A number of other references are present in the prior art that have teachings similar to those discussed above. These, however, also fail to disclose particularly the use of a polysoap or the use of such polysoap in reducing the static charge on protein fibers. However, for the purpose of completeness the following are mentioned:

The Vanderberghe U.S. Pat. No. 3,917,817 discloses hair treating cosmetic compositions containing piperazine based cationic polymer. The Sekamakas U.S. Pat. No. 4,263,189 describes the application in cosmetic formulations of cationic amine-functional copolymer condensates. The Wolfram et al. U.S. Pat. No. 4,416,297 discloses a method for durable conditioning of hair which comprises applying to hair a cationic polymer and anionic or amphoteric surfactant. Similar systems are covered by E.P. Nos. 0080976A1 and 0080977A1. The Sokol U.S. Pat. No. 4,027,008 discloses hair bleaching composition containing water soluble amino and quaternary ammonium polymers. The following additional patents describing the use of cationic polymers in hair treating compositions may also be mentioned.

U.S. Pat. No. 3,980,769-"Shampoo containing a water soluble cationic polymer", G. Ghilardi, C. Fiquet.

U.S. Pat. No. 4,217,914-"Quaternized polymer for use as a cosmetic agent in cosmetic compositions for the hair and skin," B. Jacquet, G. Lang.

The process of the present invention is applicable to a variety of protein fibers. These include such natural fibers as human hair, animal hair, wool, silk and artificial fibers such as those derived from soybean protein, casein, zein or gelatin solutions. However, it has particular utility in the treatment of human hair on the head to reduce the static charge generated there during combing and to improve its combability.

The active compounds that may be used to practice the process of the present invention are of a variety of types. Generally, they are classifiable as polysoaps and are characterized by the fact that they are quaternary ammonium salt polycations in which a long chain organic group (e.g. long chain alkyl or long chain polyether groups) are bonded as side chains to the a multitude of quaternary ammonium nitrogen atoms of the polycation. Quaternary amine polycations are high molecular weight polymers that contain amine groups scattered along the molecule either in the backbone of the polymer or in side-chains depending from the polymer backbone. The compounds that are useful herein are referred to as polysoaps because the long chain organic groups bonded to the quaternary nitrogens of the polymer as a side chain are soap-like in character.

The long chain organo groups that are bonded to the quaternary ammonium nitrogen of the polymers employed in the present invention will, preferably, be long chain hydrocarbon groups and, particularly, long chain alkyl groups. These groups will generally have at least about 12 carbon atoms in the chain and may reach as high as 22 carbon atoms. Usually, however, they will contain from about 12 to about 18 carbon atoms. As will be pointed out in more detail below the corresponding short alkyl chain quaternary ammonium salts are not useful for applicants' purposes.

As indicated above the cationic polysoaps useful in the present invention are high molecular polymeric materials. These polymeric materials may be homopolymeric, copolymeric or oligopolymeric. Generally, however, they will be homopolymers or copolymers.

It is important for the purpose of the present invention that the polymeric cationic soaps used herein carry a sufficient charge so as to be strongly substantive to the protein fibers. This can generally be insured by utilizing a polymer of high molecular weight which will have a large number of cationically charged nitrogen atoms. The molecular weight of useful polymers for the present purposes may vary over a wide range. Usually, however, this molecular weight be within the range is from about $5.10^3$ to about $10^6$ g/mol.

The cationic polysoaps of choice for use in the practice of the present invention may be defined by the various structural formulas given below:

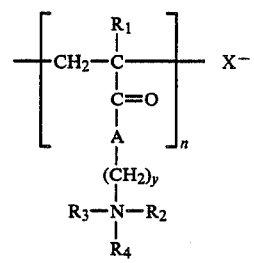

1.

wherein:
$R_1$ is H or lower alkyl having 1 to 4 carbon atoms;
$R^2$ and $R_3$ are lower alkyl having 1 to 4 carbon atoms;
$R_4$ is a long chain alkyl having at least 12 carbon atoms;
A is selected from the group consisting of —O—, and —NH—;
y is a number from 1 to 4;
n is a number designating to degree of polymerization; and
$X^-$ is an anion.

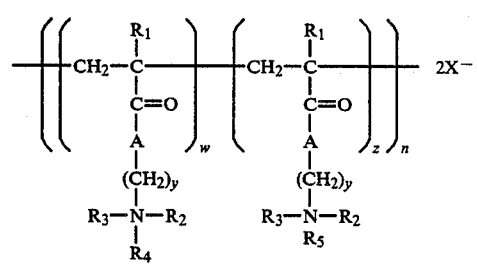

2.

wherein:
$R_1$ is H or lower alkyl having from 1 to 4 carbon atoms;
$R_2$, $R_3$ and $R_5$ are lower alkyl having 1 to 4 carbon atoms;
$R_4$ is a long chain alkyl having at least 12 carbon atoms;
A is selected from the group consisting of —O— and —NH—;
y is a number from 1 to 4;
w and z are numbers designating the number of moles of each monomer contained in the polymer;
n is a number designating the degree of polymerization; and
$X^-$ is an anion.

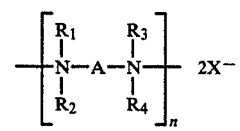

3.

wherein:
A is a divalent organo group;
$R_1$, $R_2$, $R_3$ and $R_4$ are alkyl group at least one of which is a long chain alkyl group having at least 12 carbon atoms; $X^-$ is an anion, and n designates the degree of polymerization.

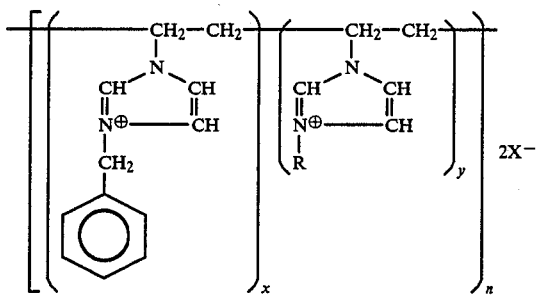

4.

wherein:
R is an alkyl radical having at least 12 carbon atoms;
x and y are numbers designating the number of moles of each monomer contained in the copolymer;
n is a number designating the degree of polymerization; and
$X^-$ is an anion.

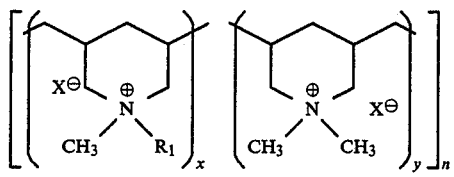

5.

wherein:
$R_1$ is an alkyl radical having at least 12 carbon atoms;
x and y are numbers designating the number of moles of each monomer contained in the copolymer;
n is a number designating the degree of polymerization; and $X^-$ is an anion.

Exemplary of the cationic polyamines that are useful in preparing the cationic polysoaps of this invention are high molecular weight polyamines such as poly(vinylpyridine), poly(vinylimidazole), poly(vinylpiperidine), poly(dimethylaminoethylmethacrylate), poly(ethylimine), poly(dimethylaminopropylmethacrylate), and the ionenes.

The cationic polysoaps used herein can be conveniently prepared by quaterizing the pre-formed polyamine, polymerization of the monomeric quaternary salts or, in the case of the ionenes, by the Menshutkin reaction. It is of interest to note that polysurfactant homopolymers have distinctly different properties from their non-surfactant analogs. The former are generally water insoluble and are applied from alcoholic solutions. The copolymerization of surfactant and non-surfactant monomers produces water or alcohol-water soluble polymers. Their antistatic activity can be easily adjusted by varying the composition of the copolymer or the length of an aklyl sidechain.

The process of the present is carried out by applying the cationic polysoap to the protein fiber surface from a composition containing the cationic polysoap. This composition will usually take the form of a liquid composition in which the cationic polysoap is distributed. However, it is also comtemplated that these compositions may also have other forms such as gels, lotions, cremes, mousses or sprays. In the usual case the vehicle for the cationic polysoap will be a solvent system in which these polysoaps are soluble or dispersible. Often this solvent system will be an aqueous, aqueous-alcoholic or alcoholic solvent system and it will be one in which the cationic polysoap is soluble.

The quantity of cationic polysoap which will be contained in the composition employed to practice the process of the present invention may vary over a range. All that is required is that it be present in sufficient concentration to significantly reduce the static charge that has been generated on the protein fiber; that is to say that all that is required is that an antistatic quantity of the cationic polysoap be contained in the treatment composition used in the process of the present invention. Generally these treatment composition may contain from about 0.1% to about 5% by weight of cationic polysoap based on the total weight of the treatment composition. Preferably, this concentration will be in the range of from about 0.2% to about 1% on the same weight basis.

In addition to the cationic polysoap the treatment compositions employed in the present process may also contain other adjuvants.

These may be any of a variety of types of materials, the only limitation being that they do not interfere with the antistatic activity of the cationic polysoaps. The adjuvants may be selected so as to improve the ease of application to the protein fiber, for stabilizing purposes, to improve the organoleptic properties of the composition, to produce a foam, and to improve other performance attributes of the formulation like ease of combing, etc. By way of example, the following adjuvants may be incorporated in the treatment compositions of this invention: anionic, cationic or amphoteric surfactants, nonionic, cationic or amphoteric polymers, hydrocarbons, silicone or other emulsions, foaming agents, etc.

In carrying out the process of the present invention the protein fibers (e.g. human hair) are saturated with the treatment composition for a period of time to allow the cationic polysoap contained in the treatment composition to be absorbed onto the fibers. This time period may vary somewhat. Usually this will be in the range of from about 10 seconds to about 20 minutes. In the preferered practice of the present process the time of treatment will be from about 1 minute to about 5 minutes.

The formulations based on the present invention can be applied as an after-treatment for dyed, bleached, waved, relaxed or untreated hair. Suitably, such formulations may contain 0.2–1% cationic polysoap and other ingredients such as buffers, color, fragrance, surfactants and preservatives.

Unless otherwise specified the following abbreviations have the meaning specified below:
PHDPM: Poly(hexadecyldimethylpropylmethacrylamide ammonium bromide).
PTDPM: Poly(tetradecyldimethylpropylmethacrylamide ammonium iodide).
PTDPM-MAPT: Co(tetradecyldimethylpropylmethacrylamide.
ammonium bromide-methacrylamidopropyltrimethyl ammonium chloride).
containing 10.3% or 23.5% tertradecyl units (by moles).
PODPM-MAPT: Co(octadecyldimethylpropylmethacrylamide
ammonium bromide-methacrylamidopropyltrimethyl ammonium chloride)
containing 15.4% octadecyl units (by moles)
12-12RI: Poly((dimethylimino)dodecylene bromide)

5-5R18: Poly((methyloctadecylimino)pentylene bromide)

PVI: Poly(vinylimidazole)

PVBI: Poly(N-vinyl-N-benzylimidazolium chloride)

PVBI-PVHI: Co(N-vinyl-N-benzylimidazolinium chloride-N-vinyl-N-hexadecylimidazolinium bromide) (1:1 molar)

PMAPTAC: Poly(methacrylamidopropyl-trimethyl ammonium chloride) MW=430,000

PDMPAMC: Poly(1,1-dimethylpiperidinium methylene chloride) MW=165,000.

To test the effectiveness of the cationic polysoap compositions employed in this invention in reducing charge generated on hair, to measure the durability of this antistatic treatment and to compare these effects with the corresponding effects obtained with comparable monomeric quaternary ammonium salts or with comparable non-soap cationic polymers the experiments described below were carried out. In addition, combing work measurements were made on some of the hair samples treated.

I. Preparation of Test Materials

Decyl, dodecyl, tetradecyl and hexadecyldimethylpropylmethacrylamide ammonium bromides were prepared by quaternization of dimethylaminopropylmethacrylamide in acetonitrile. Corresponding polymers were obtained by free radical polymerization in the bulk initiated with 2,2'-azibisisobutylonitrile (AIBN, 0.5%). Polymers with hexa and tetradecyl side chains were purified by precipitation in $H_2O$ from EtOH solutions in order to get rid of residual monomeric salts. Poly(hexadecyldimethylpropylmethacrylamide ammonium bromide) and poly(tetradecyldimethylpropylmethacrylamide ammonium iodide) had $\eta$ red=1.51 and 0.72, respectively, at 0.1 g/dl in EtOH at 25° C. Decyl and dodecyl derivatives were not purified.

II. $H_2O$ or $H_2O$-EtOH soluble copolymers poly(tetradecyldimethylpropylmethacrylamide ammonium bromide-methacrylamidopropyltrimethyl ammonium chloride) containing 10.3% and 23.5% tetradecyl units (by moles) and poly(octadecyldimethylpropylmethacrylamide ammonium bromide-methacrylamidopropyltrimethyl ammonium chloride) containing 15.4% octadecyl untis (by moles) were also prepared by polymerization initiated with AIBN.

III. Long alkyl chain ionenes poly((dimethylimino)-dodecylene bromide) (12-12R1) and poly((methyloctadecylimino)pentylene bromide) (5-5R18) were obtained by reacting equimolar amounts of appropriate diamines and dibromides in benzene at room temperature for a few days (5). 12-12R1 was soluble in $H_2O$ [$\eta$]=2.96 at 0.2 g/dl in $H_2O$, [$\eta$]=0.163 at 0.2 g/dl in 0.1M NaCl at 15 C). 5-5R18 was soluble in warm EtOH (red=0.078 at 0.2 g/dl in EtOH at 40° C.).

IV. Poly(vinylimidazole) (PVI) was prepared by benzene solution polymerization of vacuum distilled N-vinylimidazole with AIBN as initiator ([$\eta$]=0.95 in 0.1M $(CH_3)_4NCl$ EtOH at 25° C.).

V. Poly(N-vinyl-N-benzylimidazolinium chloride) (PVBI) was prepared by quaternizing PVI with an excess of benzyl chloride in DMF for 3 hours at 85° C. The polymer was precipitated by pouring the reaction mixture into acetone.

VI. Copolymer co(phenyl-N-benzylimidazolinium chloride-N-vinyl-N-hexadecylimidazolinium bromide) (PVBI-PVHI) (1:1 molar) was prepared by first quaternizing PVI with hexadecyl bromide followed by reaction with an excess of benzyl chloride at 85° C. in DMF.

VII. Poly(methacryalmidopropyltrimethyl ammonium chloride) (PMAPTAC) was prepared by $K_2S_2O_8$ initiated polymerization in $H_2O$ (Mw=430000). Poly(1,1-dimethylpiperidinium-3,5-diallyl methylene chloride) (PDMPAMC) was purchased from Calgon Corp. (Mw=165000).

Triboelectric Charging Measurements

These are measurements of the electric charge generated on hair by the combing. For the purpose of comparison both electric charge generated on hair which was treated with the test composition and hair which was left untreated were measured.

The charge generated on the hair from combing is calculated from the voltage generated on this hair. Since this voltage may be directly and conveniently measured, by the use of static detector probe and electrometer the voltages of the charged surfaces are used herein as an expression of the charge on the hair. Furthermore, it is useful to relate the voltage on the hair that has been treated to the hair that has not been treated after each has been subjected to combing. This is useful in that it will show the degree to which the treating composition has changed the static change on hair that has been combed. This relationship can be expressed as follows:

(1) relative voltage=$(V_T/V_U)$ wherein $V_T$ is the voltage measured on hair that has been given a treatment with the test composition after combing and $V_U$ is the voltage measured on hair that was not treated but after combing. As will be evident form equation (1) if the relative voltage is less than 1 (irrespective of the sign of the voltage) this will indicated that the treatment of hair with the test composition resulted in a reduction of the static charge on the hair sample.

Procedure

Test compositions were applied to shampooed virgin tresses of hair by immersion for 1 min in $H_2O$, EtOH, or $H_2O$-EtOH solutions of the respective test agents. The air fibers were then blotted with paper towels and conditioned at 25% relative humidity. The measurements of voltage of the charged surface of hair, generated by combing (10 strokes on both sides) with a nylon comb, were carried out by means of a Keithley Model 2501 Static Detector attached to a 610C Keithley Electrometer and a chart recorder. All triboelectric measurements were performed at low relative humidity of 25–30%. The relative voltage values were calculated from the relationship given above, i.e.

relative voltage=$(V_T/V_U)$

These represent the average values of three measurements on at least two tresses. For some of the treatments, concentration dependencies were obtained in order to check the consistency and reproducibility of the observed effects. As is generally true for any kind of triboelectric measurements, the reproducibility is not as good as for other physical measurements, probably because of mass transfer, surface contamination and surface abrasion during sliding contact between the comb and fiber surface. As far as the present data are concerned, it is estimated that the margin of error of relative static voltage values is about ±25%.

Combing Work Measurements

To determine dry combing work, an Instron Model 1122 Tensile Tester equipped with a Microcon I computer was used. The 65% relative humidity equilibrated tress (6.5 inches long) was first combed to remove entanglements then mounted in the Instron with hair evenly distributed across a one-inch length of a comb. The combing force was continuously recorded as the tress was combed at a speed of 10 cm/min, and its integrated value over the length of the tress was calculated as the combing work. The values of combing work reported herein represent the average of six measurements on a single tress. The results of these tests are summarized in Table I below. The symbols to the left of compounds in this table have the following meanings:

TABLE I

Values of relative static charge density and combing work for hair treated with various monomeric and polymeric ammonium salts[a]

| Quat | Relative static voltage | Combing work (Gcm) |
|---|---|---|
| ++N—decyldimethylpropylmethacrylamide ammonium iodide | 0.06 | 251 ± 60[b] |
| +Poly(N—decyldimethylpropylmethacrylamide ammonium iodide) | 0.21 | 255 ± 70 |
| ++N—dodecyldimethylpropylmethacrylamide ammonium iodide voltage | 0.11 | 179 ± 60 |
| +Poly(N—dodecyldimethylpropylmethacrylamide ammonium iodide) | −0.19 | 223 ± 53 |
| ++N—tetradecyldimethlpropylmethacrylaminde ammonium iodide | −0.31 | 359 ± 95 |
| +Poly(tetradecyldimethylpropylmethacrylamide ammonium iodide) | −0.91 | 320 ± 63 |
| ++N—hexadecyldimethylpropylmethyacrylamide ammonium bromide | −0.26 | 126 ± 30 |
| +Poly(N—hexadecyldimethylpropylmethacrylamide ammonium bromide) | −0.42 | 166 ± 20 |
| ++N—octadecyldimethylpropylmethacrylamide ammonium bromide | −0.20 | 95 ± 25 |
| +Co(tetradecyldimethylpropylmethacrylamide ammonium iodide-trimethylpropylmethacrylamide ammonium chloride) (10.3% tetradecyl units)[c] | 1.26 | — |
| +Co(tetradecyldimethylpropylmethyacrylamide ammonium iodide-trimethylpropylmethacrylamide ammonium chloride) (23.5% tetradecyl units)[d] | 0.45 (0.5 g/dl)[e] 0.76 (0.1 g/dl)[e] 1.39 (0.2 g/dl)[e] | — |
| +Co(octadecyldimethylpropylmethyacrylamide ammonium bromide-trimethylpropylmethacrylamide ammonium chloride) (15.4% octadecyl units) | 0.35 | — |
| *12-12R1 | 1.22 | — |
| +5-5R18 | −0.72 | — |
| +PVBI-PVHI | −0.29 | — |
| *PVBI | 1.03 | — |
| *PMAPTAC | 0.81 | — |
| *PDMPDAMC | 1.02 | — |
| ++Stearalkonium chloride | 0.08 | 137 ± 11 |
| untreated hair | 1.00 | 122 ± 30 |

+ = a polysoap embodied in the present invention
* = a non-soap cationic polymer
++ = a monomeric quaternary ammonium salt.
[a] monomeric and polymeric salts were applied from 1 g/dl aqueous and 0.1 g/dl ethanol solutions, respectively.
[b] standard deviation of six measurements on a single tress.
[c] applied from 25% ethanol - 75% H₂O.
[d] applied from 75% ethanol - 25% H₂O solvent system.
[e] concentration of treatment solutions.
[f] applied from 50% ethanol - 50% H₂O solvent system.

Table I lists the values of relative static voltage over combing and of combing work of hair treated with various monomeric and polymers surfactants (for comparison, the data for non-surfactant cationic polymers i.e. non-polysoaps PMAPTAC, PDMPAMC, and PVBI are also included). The data indicate that, under our conditions of treatment, all monomeric surfactants possess the ability to suppress static charge generation during combing. Surfactants with longer alkyl chains (tetradecyl, hexadecyl, octadecyl) may also reverse the sign of the generated charge.

However, polymerized surfactants show even more pronounced electron acceptor properties when deposited on the hair surface. The deposition of dodecyl, tetradecyl, and hexadecyl side chain polysoaps resulted in generation of higher density of negative charges after combing as compared to their low molecular weight analogs. Hexadecyl iodide quaternized PVI, (PVBI-PVHI) and long alkyl side-chain ionene (5-5R18) caused a similar change in the work function of hair after combing. Treatments with poly(dimethylimino)-dodecylene bromide), which contains hydrophobic moiety in the main chain, as distinguished from a side chain and other non-surfactant cationic polymers (PMAPTAC, PDMPDAMC and PVBI) did not affect the fiber work function and led to the generation of high density of positive charges.

All the above discussed polysoaps are soluble only in alcohols and are applied to hair from EtOH solutions. In order to obtain H₂O-EtOH soluble polymeric surfactants, we copolymerized tetradecyl and octa-decyldimethylpropylmethacrylamide ammonium bromide with non-surfactant trimethylpropylmethacrylamido ammonium chloride. As can be judged from the date in Table I, these copolymers produce a much smaller increase in the work function of modified fibers. The results of the tribocharging experiments indicate that the extent of surface modification can be controlled by copolymerizing non-surfactant monomeric quaternary ammonium salts with surfactant monomeric quaternary ammonium salts. For example, for the treatments with co(tetradecyldimethylpropylmetha-crylamide ammonium iodide-trimethylpropylmethacrylamide ammonium chloride) containing 10.3% and 23.5% tetradecyl units, measured relative static voltage values were 1.26 and 0.76, respectively. Similarly, incorporation of octadecyl units into the copolymer structure contributed to even more pronounced reduction of generated tribocharge (r.s.v. 0.35 for 0.1 g/dl treatment).

The triboelectric charging of hair treated with monomeric and polymeric surfactant solutions of various concentrations were also examined. FIGS. 1 and 2 of the drawings show the plots of relative voltage of hair fibers after combing as a function of the concentration of monomer and polymer treatment solution. Note that the relative voltage versus concentration dependence for polysoaps is different than that of monomeric quats. At $10^{-3}$ g/dl, polymers and their monomeric precursors exhibit little antistatic activity. Increase of the concentration of the polymer to $2 \cdot 10^{-2}$ g/dl reverses the sign of the charge generated by combing to negative. In the case of monomeric surfactants, the reversal of the sign of tribocharges is observed at higher concentration above $5 \cdot 10^{-1}$ g/dl. Similarly to their low molecular weight analogs, polymers with shorter alkyl chains (decyl and dodecyl) show diminished ability to modify fiber work function and to lower or reverse the sign of the tribocharges.

Although polymeric surfactants in general have certain advantages with respect to reducing the static charge on hair the present data generally indicates that they may increase combing work in comparison with untreated hair fiber. However, the longest alkyl chain polysoaps (e.g. poly-(hexadecyldimethylpropylacrylamide ammonium bromide) increased combing work to a lesser extent.

Durability of Antistatic Treatment

The durability of the antistatic treatment was measured by immersion of shampooed virgin tresses of hair for 1 minute in $H_2O$, EtOH or $H_2O$-EtOH solutions of the respective test agents. The fibers were then blotted with paper towels and conditioned at 25% relative humidity. A static charge was generated on each treated hair sample by combing with a nylon comb (10 strokes on both sides). Measurements of voltage of the charged surface of hair generated by the combing was carried out by means of a Keithley Model 250, Static Detector attached to a 610C Keitley Electrometer and a chart recorder. All triboelectric measurements were performed at low relative humidity of 25-30%.

Subsequent to the combing of each treated hair sample a voltage measurement was made to establish a reference base line. This was followed by shampooing the hair sample which entailed rubbing into hair a small amount of conventional anionic shampoo for 30 seconds followed by 1 minute rinse with water and then a second voltage measurement. This procedure was repeated for 4 shampooings. In each instance equivalent measurements were made on untreated hair so as to make it possible to calculate the relative voltage on the hair samples.

FIG. 3 of the drawings presents the dependence of relative voltage after combing of hair treated with poly(hexadecyldimethylpropylmethacrylamide ammonium bromide) as a function of a number of shampooings. In contrast to monomeric surfactants, which can be completely removed from the fiber surface by a single shampooing (antistatic effect disappears after the first shampooing), the effect of reversal or suppression of tribocharges achieved by the deposition of the polysoap only disappears after at least two or three shampooings. Similar behavior is exhibited by other polymeric surfactants such as poly(n-dodecyldimethylpropylmethacrylamide ammonium iodide) and co(tetradecyldimethylpropyl-methacrylamide ammonium iodide-trimethylpropylmethacrylamide ammonium chloride) (23.4% tetradecyl units). It is also noteworthy that the increase in the polymer treatment concentration retards the process of loss of the antistatic effect. In one case, 0.1 g/dl solution of high molecular weight copolymer PVBI-PVHI produced a shampoo-resistant coating which resulted in generation of slightly reduced density of negative charges during combing with a nylon comb.

What is claimed is:

1. A process for imparting an antistatic surface modification to protein fibers comprising the step of contacting the surface of the protein fibers with an anionic polymer-free composition containing an amount of a high molecular weight polymeric quaternary ammonium salt that is effective, when the composition is in contact with the protein fibers for a predetermined time period, to impart to said fibers said antistatic surface modification that is durable through at least four subsequent shampooings, said polymeric quaternary salt having as a substituent of the ammonium radical an alkyl group of at least 12 carbons.

2. A process according to claim 1 wherein said alkyl group contains from 12 to 18 carbon atoms.

3. A process according to claims 1 or 2 wherein said composition comprises a liquid vehicle in which is distributed said quaternary ammonium salt, said liquid vehicle being selected from the group consisting of water, ethyl alcohol and mixtures thereof.

4. A process according to claims 1 or 2 wherein said quaternary ammonium salt is contained in said composition at a concentration in the range of from about 0.1% to about 5% by weight based on the total weight of said composition.

5. A process according to claims 1 or 2 wherein said protein fiber is human hair on the head.

6. A process according to claims 1 or 2 wherein said composition consists essentially of a solution of said quaternary ammonium salt in a solvent system selected from the group consisting of water, ethyl alcohol and mixtures thereof.

7. A process according to claim 1 wherein said quaternary ammonium salt corresponds to the formula

(I)

wherein:

$R_1$ is H or lower alkyl having 1 to 4 carbon atoms;

$R_2$ and $R_3$ or lower alkyl having 1 to 4 carbon atoms;

$R_4$ is a long chain alkyl having at least 12 carbon atoms;

A is selected from the group consisting of —O— or —NH—;

y is a number from 1 to 4;

n is a number designating the degree of polymerization; and $X^-$ is an anion.

8. A process according to claim 7 wherein $R_1$ is a methyl;

$R_2$ and $R_3$ are methyl;

$R_4$ is alkyl having from 12 to 18 carbon atoms;

A is —NH—;

y is 3; and $X^{-1}$ is a halide.

9. A process according the claim 1 wherein said quaternary ammonium salt is a copolymer which corresponds to the formula

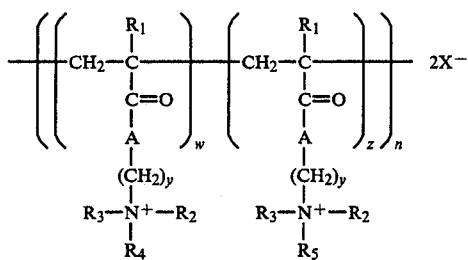

II wherein:
R₁ is H or lower alkyl having from 1 to 4 carbon atoms;
R₂, R₃ and R₅ are lower alkyl having 1 to 4 carbon atoms;
R₄ is a long chain alkyl having at least 12 carbon atoms;
A is selected from the group consisting of —O—, or —NH—;
y is a number from 1 to 4;
w and z are numbers designating the number of moles of each monomer contained in the polymer;
n is a number designating the degree of polymerization; and
$X^-$ is an anion.

10. A process according to claim 9 wherein:
R₁ is methyl;
R₂, R₃ and R₅ are methyl;
R₄ allkyl having 12 to 18 carbon atoms;
y is 2; and
$X^-$ is halide.

11. A process according to claim 1 wherein said quaternary ammonium salt corresponds to a formula

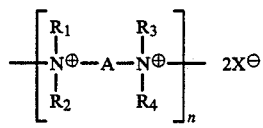

III wherein:
A is a divalent organo group;
R₁, R₂, R₃ and R₄ are alkyl group at least one of which is a long chain alkyl group having at least 12 carbon atoms;
$X^-$ is an anion, and n designates the degree of polymerization.

12. A process according to claim 11 wherein: A is a divalent alkylene group having from about 2 to 12 carbons atoms; at least one of R₁, R₂, R₃ or R₄ being a long claim alkyl groups having 12 to 18 carbon atoms, the remainder being lower alkyl groups having 1 to 4 carbon atoms.

13. A process according to claim 1 wherein said quaternary ammonium salt is a copolymer corresponding to the formula

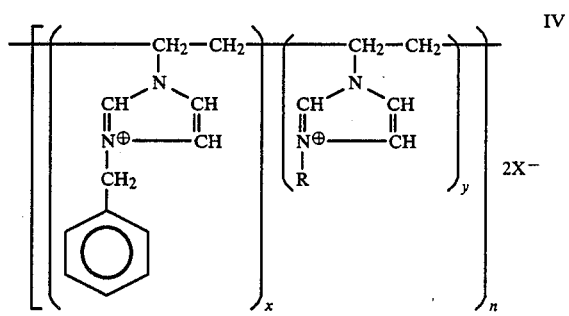

IV wherein:
R is an alkyl radical having at least 12 carbon atoms;
x and y are numbers designating the number of moles of each monomer contained in the copolymer;
n is a number designating the degree of polymerization; and
$X^-$ is an anion.

14. A process according to claim 13 wherein:
R is an alkyl having from about 12 to 18 carbon atoms; and $X^-$ is a halide.

15. A process according to claim 1 wherein said quaternary ammonium salt is a copolymer according to the formula:

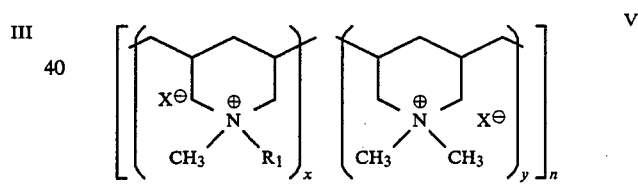

V wherein R₁ is an alkyl having at least 12 carbon atoms; x and y are numbers designating the number of moles of each monomer contained in the copolymer; $X^-$ is an anion, and n is a number designating the degree of polymerization.

* * * * *